United States Patent [19]

Anderson et al.

[11] Patent Number: 5,160,700

[45] Date of Patent: * Nov. 3, 1992

[54] STERILIZING SYSTEM AND METHOD

[75] Inventors: Harold W. Anderson, Oyster Bay, N.Y.; Charles H. Harrison, Haw River, N.C.

[73] Assignee: H. W. Andersen Products, Inc., Oyster Bay, N.Y.

[*] Notice: The portion of the term of this patent subsequent to Jun. 26, 2007 has been disclaimed.

[21] Appl. No.: 636,838

[22] Filed: Jan. 2, 1991

Related U.S. Application Data

[63] Continuation-in-part of Ser. No. 416,896, Oct. 4, 1989, Pat. No. 5,082,636.

[51] Int. Cl.$^5$ .............................................. A61L 2/00
[52] U.S. Cl. ........................................ 422/34; 422/1; 422/28; 422/294; 239/55
[58] Field of Search .................. 422/34, 119, 124, 294, 422/300, 307, 1, 28; 239/55

[56] References Cited

U.S. PATENT DOCUMENTS

| 3,476,506 | 11/1969 | Andersen et al. | 422/29 |
| 4,590,037 | 5/1986 | Kaye | 422/116 |
| 4,671,936 | 6/1987 | Barron | 422/30 |
| 4,770,851 | 9/1988 | Joslyn | 422/26 |
| 4,909,999 | 3/1990 | Cummings et al. | 422/298 |
| 4,937,046 | 6/1990 | Andersen et al. | 422/33 |
| 5,082,636 | 1/1992 | Andersen | 422/294 |

Primary Examiner—Lynn M. Kummert
Assistant Examiner—Krisanne M. Thornton
Attorney, Agent, or Firm—Jordan and Hamburg

[57] ABSTRACT

A sterilizing system includes a sealed container releasably containing a gaseous sterilant under pressure and a first enclosure made at least partially of a gas-permeable material. The container and the articles to be sterilized are disposed in and sealed within the first enclosure, the container while in the sealed first enclosure being manipulatable to release gaseous sterilant into the sealed first enclosure. A second enclosure in which the first enclosure is disposed is constructed such that the sterilant released into the first enclosure from the container diffuses through the gas-permeable material of the first enclosure into the second enclosure at a rate capable of establishing sterilizing conditions in the first enclosure during a sterilizing cycle to thereby effect sterilization of the articles in the first enclosure. A moisture-releasing humidifying device is disposed within the first enclosure for releasing moisture into the first enclosure during the sterilization cycle, and a regulating system comprising an exhaust device is operable to exhaust the sterilant gas from the second enclosure to minimize the amount of sterilant gas in the second enclosure, thereby providing for minimized residue sterilant in the surrounding work area.

22 Claims, 6 Drawing Sheets

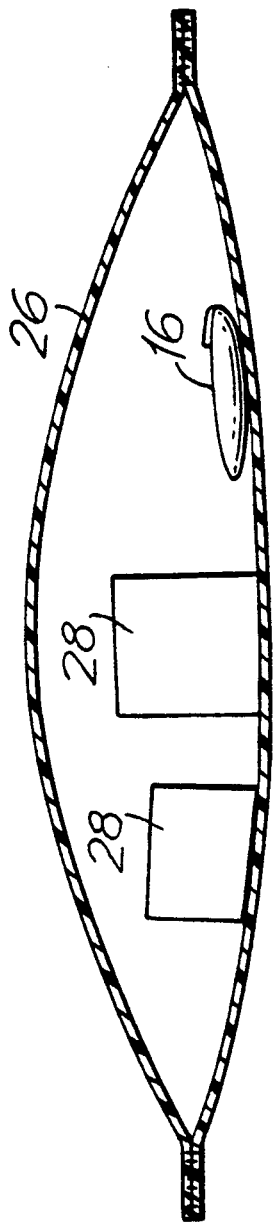
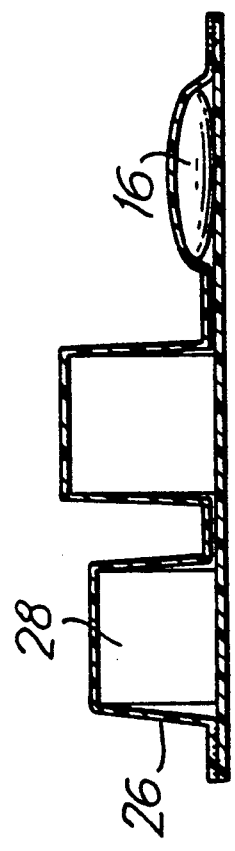

STERILIZING SYSTEM AND METHOD

This is a continuation-in-part application of U.S. Ser. No. 07/416,896, filed Oct. 4, 1989, now U.S. Pat. No. 5,082,636 issued Jan. 21, 1992.

This invention relates to a sterilize system and method for sterilizing surgical, medical, dental and other instruments, tools, apparatus, and the like using a gaseous sterilant.

BACKGROUND OF THE INVENTION

A prior art sterilization system is described in U.S. Pat. No. 3,476,506, issued Nov. 4, 1969. This prior art patent discloses an ampule or source sterilant, a gas release bag which contains the ampule, a liner bag which contains the gas release bag and the items to be sterilized, and a metal container which contains the liner bag. Ethylene oxide sterilizing gas from the ampule is released into the gas release bag and the sterilization gas in the gas release bag is released into the liner bag to sterilize items within the liner bag. After a period of time (e.g. 4 hours), virtually all of the gas that is contained within the ampule is diffused from the inside of the gas release bag into the liner bag where it held in contact with the items to be sterilized for the duration of the sterilizing cycle (e.g. 12 hours). During this time, a significant portion of the gas is gradually released by the liner bag gas diffusion membrane into the space between the liner bag and the metal container, and the gas escapes from the unsealed metal container into the ambient work area.

This gas sterilization system is marketed commercially by H. W. Andersen Products, Inc. under the registered trademark ANPROLENE® and is disclosed in the aforementioned U.S. Pat. No. 3,476,506, the contents of which are incorporated herein by reference.

One problem with this prior art sterilization system is that the operator is exposed to the sterilizing gas in the work area and to the gas in the liner bag when the latter is opened upon completion of the sterilization cycle. One attempt to overcome this problem is set forth in the present Assignee's U.S. Pat. No. 4,937,046, issued Jun. 26, 1990, entitled "Sterilization System and Method" which discloses utilizing a post-sterilization flush which minimizes the extent of residue sterilant in the surrounding work area.

In another prior art gas sterilizer, described in U.S. Pat. Nos. 3,516,223 and 3,630,665 and marketed commercially by H. W. Andersen Products, Inc. under the registered trademark STERIJET®, the items to be sterilized are prepared by washing and drying in the same manner as for the previously-described sterilization system. These items are then wrapped in paper or cloth and placed in a bag having a permeable membrane. The bag is placed over a spout extending between jaws of a sterilizing device and air is pumped from the bag until the bag appears to be vacuum-tight around the enclosed items. An appropriate dose of sterilizing gas is then injected into the bag.

An impulse of electric current is passed through a heating wire carried on one of the jaws, and the heating wire heats the bag to a temperature sufficient to fuse the bag but below the ignition temperature of the sterilant to thereby form a seal.

The sealed bag containing the items to be sterilized and the sterilizing gas is then placed in a heated and ventilated aerator chamber where it remains for at least 12 hours. By way of example, the aerator chamber may be heated to 50° C. During this time, the gas sterilizes the contents of the bag and then diffuses through the permeable membrane of the bag into the aerator chamber where it is evacuated by a ventilator. Since the material from which the bag is fabricated is permeable to the sterilizing gas and impermeable to air, the vacuum initially provided in the bag reappears as the gaseous sterilant diffuses out of the bag, giving the bag a finished and a characteristic vacuum-tight appearance of a sterile package. A sterilizing system of this type is disclosed in the aforementioned U.S. Pat. Nos. 3,516,223 and 3,630,665, the contents of which are incorporated herein by reference.

Unlike the first system described heretofore, the second system does not use pre-measured, unit doses of ethylene oxide sterilant. Also, the second system is a more expensive system to buy and to maintain than the first system.

It has been widely recognized for many years by those skilled in the art and science of sterilization with gases such as ethylene oxide that the sterilization gas is more effective in killing microorganisms if those microorganisms are normally hydrated and, further, if the sterilization process is carried out in an atmosphere which contains at least 30% relative humidity.

SUMMARY OF THE INVENTION

According to the present invention, there is disclosed a sterilization method in which operator exposure to the sterilant gas is precluded, the system being capable of utilizing a relatively economical and adaptable system of releasing the sterilant from sealed pre-measured doses into a sealed enclosure or bag containing the articles to be sterilized while assuring the maintenance of hydration of the contents of the enclosure during the sterilization process regardless of the ambient relative humidity.

According to the present invention, an apparatus for use with the sterilizing system includes a sterilant gas release means in the form of a sealed container (for example, a glass ampule) releasably containing a gaseous sterilant under pressure. The sealed container is disposed within a pouch such as a paper envelope or the like. An enclosure such as a plastic bag made at least partially of a gas-permeable membrane (for example, plastic film) is provided and the sealed sterilant container along with the articles to be sterilized, a humidifying device and a sterilization indicator are placed in the enclosure and the latter is then sealed.

The sterilant which is characterized by toxicity and flammability when released from its sealed container is releasable into the enclosure to effect sterilization of the articles in the sealed enclosure. A cabinet or chamber is provided in which the sealed enclosure containing the sterilant, the articles to be sterilized, the humidifying device, and the sterilization indicator are placed. Just before the sealed enclosure is placed in the chamber, the sterilant is released from the container by manual manipulation of the sealed sterilant container through the walls of the hermetically sealed enclosure and the sterilant gas is thereby released from its container and released to the inside of the sealed enclosure which contains the articles to be sterilized, the humidifying device and the sterilization indicator. The sealed enclosure is then placed in the chamber and the chamber is sealed from the outside atmosphere. The sterilization thereafter takes effect while the sealed enclosure is disposed within the closed chamber. The chamber is heated, for example, to 50° C., and also the chamber is aerated and ventilated to the outside atmosphere. Since sterilization takes effect while the sealed enclosure is within the aerated and ventilated chamber, operator exposure to the sterilant is nil. Both sterilization and aeration of the chamber are effected while the chamber is closed such that in both operations, operator exposure to the sterilant is precluded. The humidifying device, within the sealed enclosure, assures maintenance of hydration of the contents of the sealed enclosure containing the articles to be sterilized. The sterilization indicator within the sealed enclosure provides an indication of the actual dose of sterilant delivered by the sterilant ampule.

BRIEF DESCRIPTION OF THE DRAWINGS

FIG. 3 is an elevational sectional view of the first enclosure 26 shown in FIG. 1.

FIG. 4 is an elevational sectional view similar to FIG. 3 showing an alternate embodiment.

DESCRIPTION OF THE PREFERRED EMBODIMENTS

Figure 6:
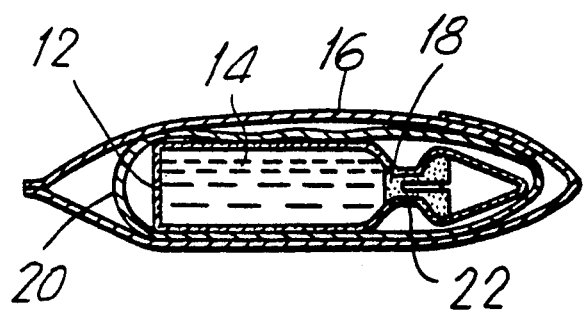
FIG. 6 is a sectional view taken along the line 6—6 in FIG. 5.

Referring to the drawings, and particularly to FIG. 6, a sterilant release means in the form of a glass ampule 12 contains a source of sterilant 14. The ampule 12 contains, for example, ethylene oxide in a liquid state which escapes into an envelope 16 when the ampule 12 is intentionally broken as will be further described. Ampule 12 has a sealed portion 18 which is sealed after the ethylene oxide 14 is deposited inside the ampule 12 during manufacture of the ampule. The ampule 12 is wrapped in a wrapping material 20 (e.g., paper toweling) and placed in the envelope 16, which may be made of paper. The envelope 16 is then closed, for example, by closing one of its end portions with adhesive or the like. Ampule 12 has a narrow neck 22 which has a score line. As will be further described, the narrow neck 22 is broken manually at the score line in order to release ethylene oxide gas into the envelope 16. The paper toweling 20 and the envelope 16 prevent broken glass and sharp edges from coming into contact with other parts of the sterilizing apparatus.

Envelope 16 is made of paper or other material which is readily permeable to the ethylene gas so as to release the gaseous ethylene oxide into a bag or enclosure 26 (FIG. 3), into which the envelope 16 is placed in order to sterilize articles 28 disposed within the enclosure 26. The gaseous sterilant passes readily through the interstices of the paper envelope 16 such that the concentration of the gaseous sterilant in the enclosure 26 rises within minutes to a peak concentration. Although the enclosure 26 is a gas diffusion membrane, the enclosure 26 retains the sterilant long enough to sterilize its contents and then allows the gas to diffuse through the membrane into a second enclosure in the form of a cabinet or chamber 29 (FIG. 1) into which the enclosure 26 is placed and from which the sterilant is exhausted as will be further described.

Figure 2:
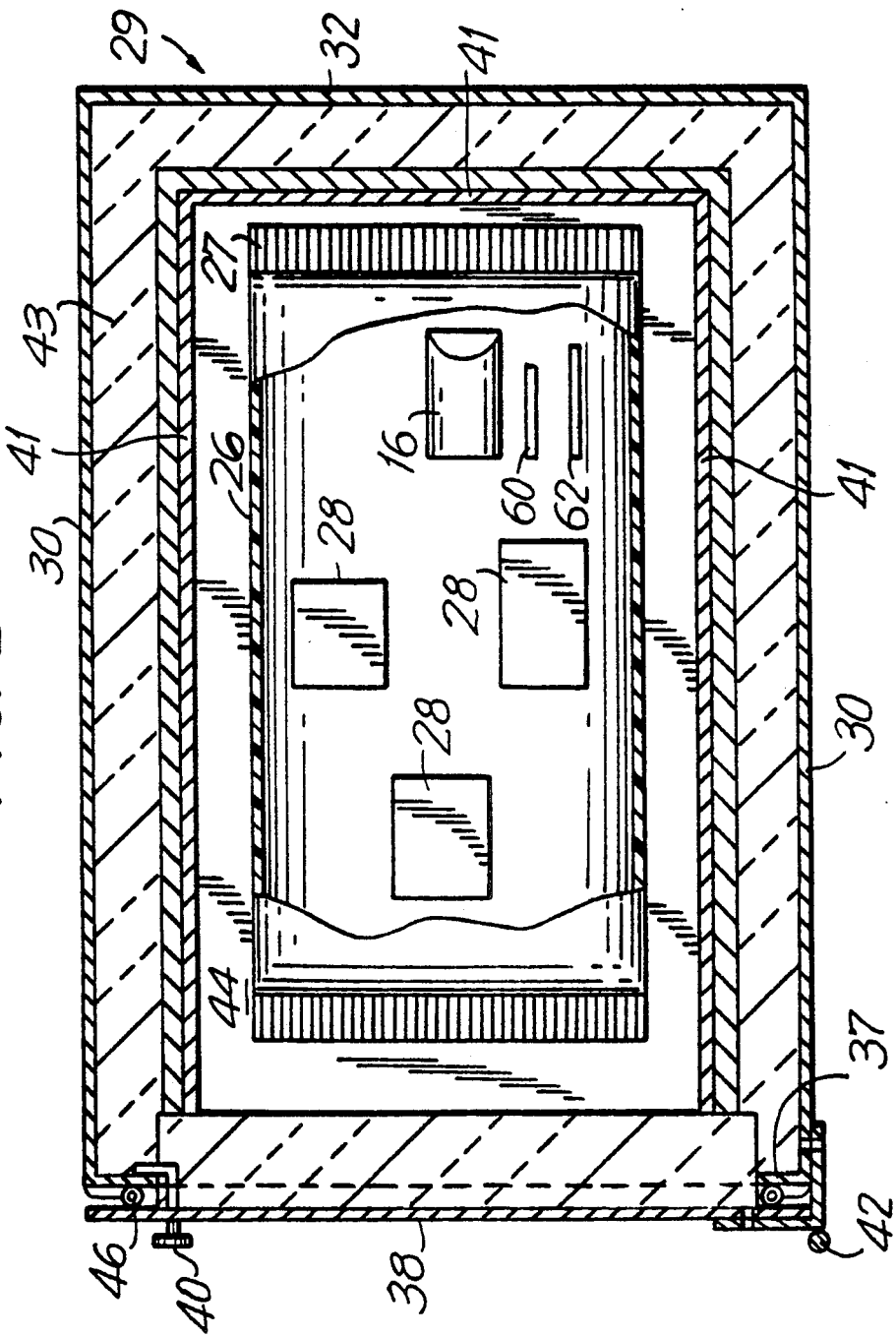
FIG. 2 is a partial sectional view taken along the line 2—2 in FIG. 1.
Figure 5:
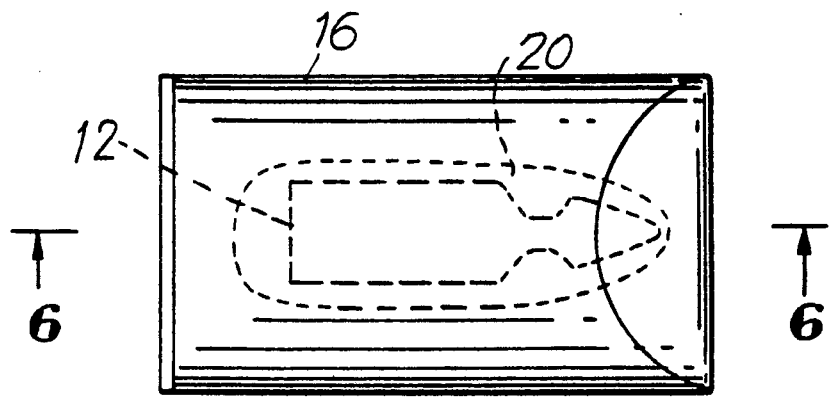
FIG. 5 is a top view of the sealed container which contains the sterilant gas.

Chamber 29 has side walls 30 (FIG. 2), a rear wall 32, a top wall 34, a bottom wall 36, and a front wall 37 which has an opening with a door 38. Door 38 has a handle and lock 40 along with hinges 42. The inner compartment 44 is sealed gas-tight, for example by gasket 46. Chamber 29 is normally maintained at a negative pressure or less than atmospheric pressure by an exhaust system as will be further described.

The chamber 29 is heated and thermostatically controlled to assure an internal temperature of about 50° C. The heating may be effected by electric plate heaters 41 disposed on the inside of the various walls of the chamber 29. The chamber 29 is insulated as indicated at 43. Circulation within the chamber 29 is effected by a motor driven fan 37 disposed within a protective screen 39.

Air and gas exhaust means includes an exhaust conduit 50 and an exhaust fan 48. An outlet opening 49 in the chamber 29 leads to the exhaust conduit 50. A building 51 has a wall 52 with an opening through which the exhaust fan 48 exhausts the air and sterilant gas to the outside atmosphere outside of the building 51.

Figure 7:
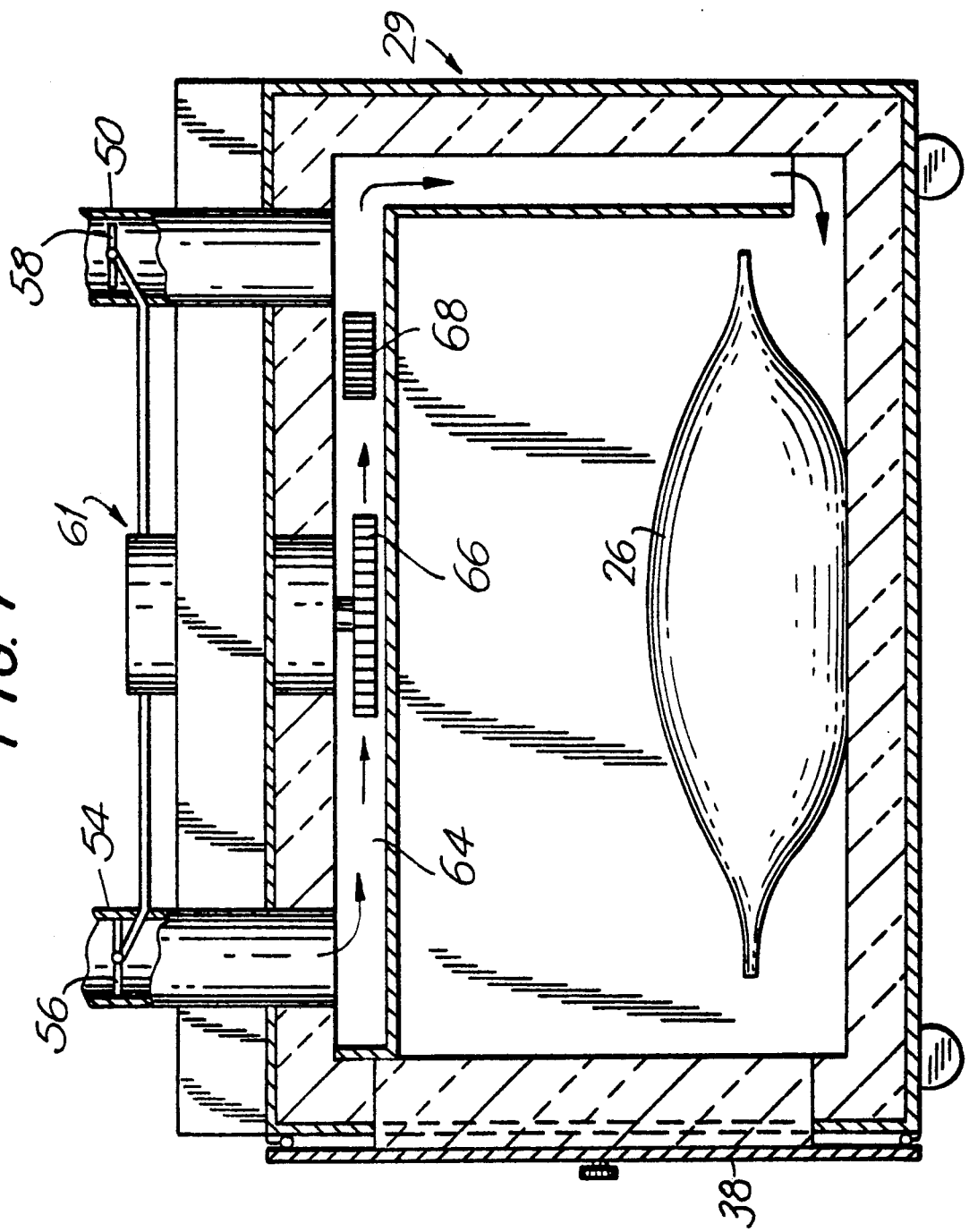
FIG. 7 is a view similar to FIG. 1 showing an alternate embodiment.

FIG. 7 shows an alternate arrangement of the chamber 29 wherein an internal duct 64 is provided and a fan 66 is provided in the duct 64 to circulate the sterilizing gas. Instead of wall heaters, an electric heater 68 is provided in the duct 64.

Figure 1:
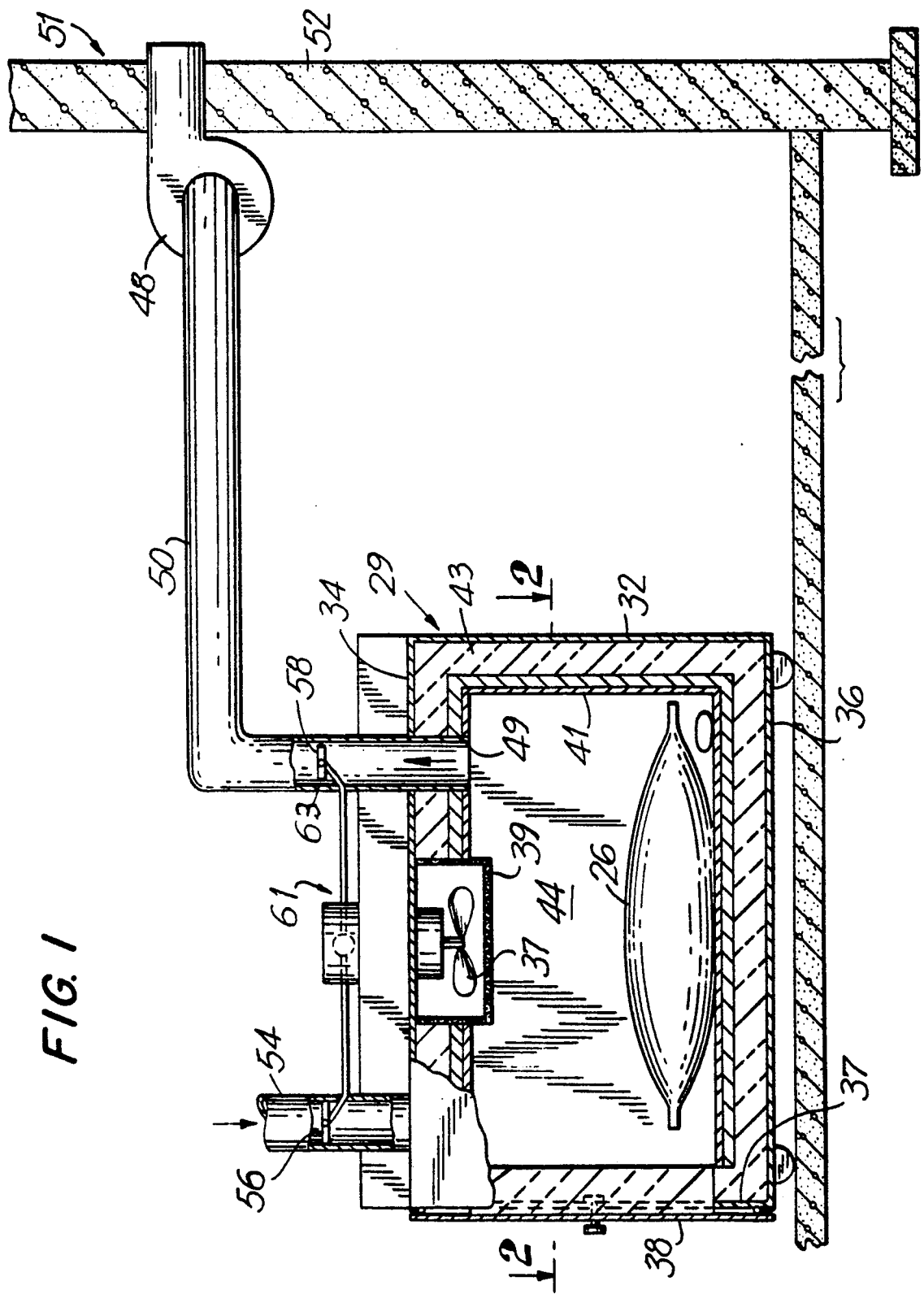
FIG. 1 is an elevational view of a sterilization system according to one embodiment of the invention.

As shown in FIG. 1, an air inlet conduit 54 leads to the inner compartment 44 for introducing air into the inner compartment 44. An inlet valve 56, for example a butterfly valve, is provided in the air inlet conduit 54. Also an exhaust valve 58, for example a butterfly valve, is provided in the exhaust conduit 50. The air inlet valve 56 and the exhaust valve 58 are mechanically linked by interconnect means or linkage 61 such that both the air inlet valve 56 and exhaust valve 58 operate in unison. Thus, when one valve is in its closed position, the other valve is also in its closed position. Also, when one valve is in its open position, the other valve is in its open position. The air inlet valve 56 when in its closed position, tightly seals off the air inlet conduit 54. However, when the exhaust valve 58 is in its closed position, the exhaust valve 58 does not provide a complete seal but provides a flow passage, shown at 63 in FIG. 1, to permit exhausting of the chamber 29 when the exhaust valve 58 is in its closed position for reasons which will be further explained.

The articles 28 to be sterilized are prepared for sterilization by first being disassembled, washed, dried and individually wrapped in gas-permeable wrapping, for example paper.

A sterilization cycle starts by placing the wrapped articles 28 to be sterilized, an envelope 16 containing an unopened ampule 12, a moisture-releasing humidifying device 60, and a sterilizing indicator 62 into the unsealed enclosure 26. As will be further described, the humidifying device 60 will maintain the contents of the enclosure 26 at a relative humidity of greater than 30% at 50° C. Also, as will be further described, the sterilizing indicator 62 will indicate the dose of sterilization delivered at the end of the sterilizing cycle. The enclosure 26 is hermetically heat-sealed, for example at 27, such as by a known electric impulse heater. Just before the enclosure 26 is placed in the chamber 29, which has been purged as will be further described, the enclosure 26 is manually manipulated through its hermetically sealed walls and the walls of the envelope 16 to break the ampule 12 at the narrow neck 22, whereupon pure ethylene oxide gas is released to the inside of the paper envelope 16, and then passes through the interstices of the paper envelope 16 into the enclosure 26. Because the envelope 16 is made of paper, the concentration of ethylene oxide in the enclosure 26 rises within minutes to the desired peak concentration.

As soon as the ampule 12 is broken and the ethylene gas is released, the enclosure 26 and its contents are placed in the already purged chamber 29 and the door 38 is closed. The sterilizing gas that is released within the enclosure 26 is held in contact with the articles 28, to be sterilized for the duration of the sterilizing cycle (e.g., 16 hours) during which the enclosure 26 is disposed in the chamber 29. During this time, a significant portion of the sterilizing gas is gradually released through the gas permeable walls of the enclosure 26 into chamber 29. Chamber 29 is maintained at a negative pressure due to the operation of the exhaust fan 48 and the passage 62 past the exhaust valve 58 so that none of the slowly-diffusing gas from the enclosure 26 is allowed to escape into the surrounding work area. Thus, the sterilizing gas in chamber 26 is exhausted to the outside atmosphere outside the building 51 through the exhaust conduit 50 and the exhaust fan 48.

The enclosure 26 is left in the sterilizing chamber 29 for approximately 16 hours at 50° C. The ampule 12 will deliver a dose of at least 500 mg-hours per liter to the contents of the enclosure 26. This dose will kill the most resistant spores known at 50° C. within the 16-hour cycle, providing that the spores have been rehydrated, such rehydration being effected by the humidifying device 60. The ethylene oxide concentration peaks at about 100,000 ppm in the enclosure 26 and then, since the enclosure 26 is permeable to the ethylene oxide, the concentration falls asymptotically to an end-of-cycle concentration of about 2,000 ppm. At the end of the sterilizing cycle, the chamber 29 is purged to reduce the concentration of ethylene oxide in the chamber 2 to a post-purge concentration of about 1 ppm,, making it possible for an operator to safely open the door 38.

The purging of the chamber 29 at the end of the sterilization cycle is initiated by pressing a purge-cycle button to start the chamber purge cycle. When this is done, the exhaust valve 58 in the exhaust conduit 50 opens the interior of the chamber 29 to the exhaust conduit 50 and the air inlet valve 56 on the inlet conduit 58 also opens, allowing a large volume of room air to be easily drawn into and through the chamber 29 and out the exhaust conduit 50, exhausting, finally, to the outside of the building 51. This purge cycle sharply lowers the concentration of ethylene oxide in the sterilizing chamber 29 from an idling concentration of about 50 ppm to a post-purge concentration in about two minutes of about 1.0 ppm, making it possible for an operator to safely open the chamber 29 even though there are enclosures 26 containing the sterilant still in the chamber 29 from the previous sterilization cycle.

The temperature in the chamber 29 is maintained at a nominal temperature of 50° C. by the thermostatically controlled heaters 41. During the purge cycle or when the chamber door 38 is opened, the 50° C. nominal temperature of the atmosphere in the chamber 29 falls rapidly but, as soon as the door 38 is closed and the purge cycle ends, a thermostat in the interior of the chamber 29 plus the effect of forced internal air circulation by the motor driven fan 37 helps the heaters 41 to bring the chamber 29 back to 50° C. very quickly, for example 3 to 5 minutes.

At the end of the post-purge cycle, the door 38 of the chamber 29 is opened and the enclosures 26 containing the sterile articles 28 are removed from the chamber 29. The sterilization indicator 62 which may be viewed through the transparent enclosure 26 will indicate the actual dose of the sterilant delivered by the sterilant ampule.

The enclosure may be placed, unopened, on a shelf, or opened, and the contents used, as sterile, without fear of operator exposure to toxic levels of ethylene oxide.

A dual volume exhaust control system may be provided in which low volume exhaust occurs during the sterilizing cycle for economy and high volume exhaust occurs for purging just before opening the door.

The enclosure 26 containing the items to be sterilized may be sealed in a vacuum sealer which withdraws the air from the enclosure to thereby create a vacuum in the enclosure 26. Removing the excess air from the enclosure assures faster penetration of the load by the sterilant and also provides a vacuum-tight appearing package at the end of the sterilizing cycle such as shown in FIG. 4. If the enclosure 26 is initially vacuum sealed, the fact that the enclosure is initially vacuum sealed will also indicate that the sterilization has been satisfactorily accomplished and the contents of the vacuum sealed enclosure may be considered sterile as long as the enclosure 26 appears vacuum tight.

Figure 8:
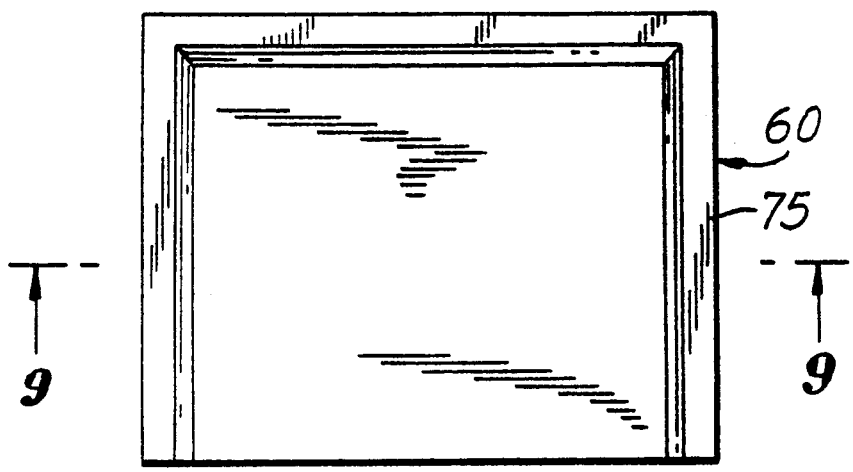
FIG. 8 is a view of a moisture-releasing dehumidifying device.
Figure 9:
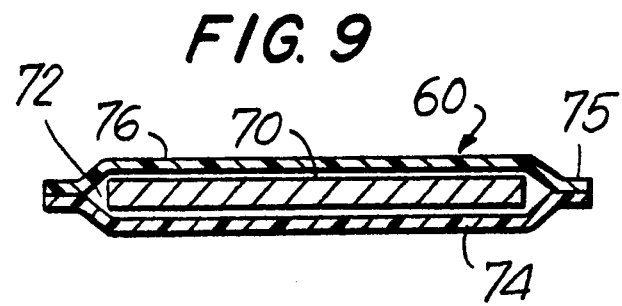
FIG. 9 is a sectional view taken along the line 9—9 in FIG. 8.

As shown in FIGS. 8 and 9, the humidifying device 60 is constructed of an inner layer or wafer 70 of a water-absorbent material sandwiched and enclosed within a sealed enclosure 2 formed between outer layers 74 and 76 of a water vapor-permeable and hydrophobic material. By way of example, the wafer 70 may be approximately one inch or two inches square and may be made of a water-absorbent material having a thickness, for example, of 3/32 to ⅛ inch, and an absorbency resulting in a carrying capacity of about 500 mg of water such that the outside of the device 60 does not feel wet to the touch. Wafer 70 is preferably made of paper, such as pressed paper, cardboard, blotter paper and the like, but can be constructed of other materials having the ability to absorb water. Outer layers 74 and 76 are made of a hydrophobic and water-permeable material such as spun bonded plastic fibers of polyethylene or polyolefin, an example of such material being sold by E.I. du Pont de Nemours & Co. under the trademark TYVEK. The hydrophobic but water-vapor-permeable outer layers 74 and 76 are sealed around the edges 75 to completely encase inner wafer 70 and function to prevent the damp inner wafer 70 from directly contacting items to be sterilized during the gas sterilization process. This is advantageous because many items to be sterilized might otherwise be damaged by prolonged contact with a wet surface.

The wafer 70 is impregnated with water before it is sealed in the water-permeable material 74,76. Alternatively, alcohol may be added to the water. The water-permeable material 74,76 has interstices which provide pathways for moisture to pass out of the sealed enclosure. However, as previously indicated, the outside of the device 60 does not feel wet to the touch, thereby precluding undesired contact of items to be sterilized with a wet surface. Even though the device does not transmit water directly to the articles to be sterilized with which it is placed, sufficient moisture escapes through the interstices of the enclosure material 74,76 to provide the desired humidity within the enclosure 26 in which the device 60 is placed along with the articles 28 to be sterilized. After the wafer 70 have been impregnated with water and sealed within the enclosure 72, the devices 60 may be stored in sealed containers, such as closed glass jars, until ready for use.

The humidifying device of FIGS. 8 and 9 thus provide a small and inexpensive device that can be sealed in to the enclosure 26 along with the articles to be sterilized when preparing for gas sterilization.

In operation, the humidifying device 60 acts to maintain the requisite humidity within the enclosure 26 throughout the sterilization process, thereby maintaining the necessary hydration of microorganisms within the enclosure 26. In this regard, without the humidifying device 60, the contents of the enclosure 26 will be exposed to sharply declining relative humidity as the temperature increases. Typically, the relative humidity will decline by 50% for every 10° C. rise in temperature.

It is well-known that a liter of air at 20° C. which is saturated with water (100% relative humidity) contains approximately 17 mg of water. At 30° C., a liter of saturated air contains approximately 32 mg of water, at 40° C. it contains approximately 60 mg of water, and at 50° C. it contains approximately 100 mg of water.

When placed in a water-impermeable plastic sterilization enclosure 26, the humidifying device 60 containing approximately 500 mg of water, will add about 1% relative humidity to the enclosure per minute of exposure up to about 80% relative humidity. Thereafter, humidification proceeds at a slower rate until 100% relative humidity is achieved. Moreover, one humidifying device 50 will bring the relative humidity of a five-liter enclosure 26 to 50%, even if the initial humidity within the sealed enclosed is 0%. Further, at 20° C., a single humidifying device 60 carrying about 500 mg of water is capable of fully humidifying (100% relative humidity) 29.4 liters of dry air.

It is preferred that the humidifying device 60 be capable of absorbing and carrying approximately 500 mg of water, wherein it is damp but not wet to the touch. Further, it is preferred that the device 60 actually be provided with about 500 mg of water before use. This results in a humidifying device 60 which is able to achieve the objective of the invention. However, the size of the device 70 and its water absorption capacity are variable. For example, a humidifying device having a water absorption capacity of 250 mg can be employed. If needed, two or more of such devices 60 can be used simultaneously to provide the necessary humidifying capacity for a single enclosure.

The shape of the humidifying device is preferably square as shown in the drawings. However, other shapes such as a circular, oval, rectangular, etc. may be used, as long as the shape permits easy insertion into gas sterilization enclosure 26.

In operation, water may be allowed to evaporate from the device 60 through the hydrophobic and water vapor-permeable outer layers 74 and 76 into the enclosure 26 to raise the relative humidity to the required level. Gas release is then effected as previously described.

As regards heating of the contents of the enclosure 26 during the sterilizing cycle, water will continue to evaporate from the humidifying device 60 during the heating to maintain the relative humidity in the enclosure 26 at or above the required level.

The humidifying device 60 maintains microorganisms within the enclosure 26 in a hydrated state suitable for efficient gas sterilization. Moreover, the arrangement is self-correcting in that as the temperature within the water-impermeable enclosure 26 increases, thus potentially decreasing the relative humidity, the rate at which water evaporates from the humidifying device 60 into the enclosure 26 increases, thus maintaining the relative humidity within the enclosure and preventing the decrease which would otherwise occur. Conversely, as the relative humidity in the enclosure 26 increases, the rate of evaporation of water from the humidifying device 60 decreases.

Inhibitors to microbial growth such as chlorine, sodium benzoate, salt (NaCl) and others may be added to the water which is absorbed by the wafer 70 to eliminate mold on the humidifying device. A 5% salt solution, for example, will eliminate any such mold without affecting the rate of humidification.

Vacuum dehydration, chemical desiccation or prolonged exposure to ambient relative humidity below 30% has been demonstrated to produce spores highly resistant to sterilization by ethylene oxide gas. Rehydration of spores so changed, and hence reversion to normal sensitivity, does not seem to occur until they have been actually wetted or placed in a 100% relative humidity atmosphere. If the nature of the articles to be sterilized is such that these water treatments are harmful, then pre-treatment in the chamber 29 having a saturated humidity at 50° C. can be performed for an overall pre-treatment procedure as follows:

The articles to be sterilized are wrapped in paper or cloth in the usual manner and placed in the enclosure 26 along with the unopened ampule 12, the humidifying device 60 and the sterilizing indicator 62. The enclosure 26 is sealed and, without breaking the ampule, the sealed enclosure 26 is placed in the chamber 29. After about 4 hours, the sealed enclosure 26 is removed from the chamber 29 and left at room temperature for about 4 hours. Since the chamber is maintained at a nominal temperature of 50° C., the sealed enclosure 26 is heated while in the chamber 29 thereby causing water to evaporate from the humidifying device 60. Subsequently, when removed from the heater chamber 29 and allowed to cool in the ambient air, the inside of the enclosure becomes saturated with moisture. After the aforesaid cooling for about 4 hours, the ampule 2 is broken to release the gaseous sterilant into the sealed enclosure 26, which is now saturated with moisture, and the enclosure is placed in the chamber 29 to start the sterilizing cycle as previously described.

The sterilization indicator 62 may be of the type disclosed in U.S. Pat. No. 4,145,186, issued Mar. 20, 1979, to the present Assignee and sold under the Trademark DOSIMETER ®. As an alternative embodiment, the sterilization indicator 62 may not be used.

Alternatively, two ducts may be provided between the sterilizing chamber and the outside atmosphere, one for exhausting the chamber and one for providing outside air makeup.

As an alternate arrangement, the sterilizer chamber may be provided with a plurality of inner doors, for example, one door per shelf, so that the problem of maintaining adequate ventilation when the main door is open is made easier.

If multiple small packages are being sterilized in a large enclosure, more rapid and more complete aeration will occur if the larger package is opened at 12 hours and the smaller packages are allowed to air in the sterilizing chamber but outside the enclosure.

Although the invention is illustrated and described in relationship to specific embodiments, it is nevertheless not intended to be limited to the details shown, since various modifications and structural changes may be made therein without departing from the spirit of the invention and with the scope and range of equivalents of the claims.

What we claim is:

1. Apparatus for sterilizing articles with a sterilant characterized by toxicity and flammability, said apparatus comprising a sealed container means releasably containing a gaseous sterilant under pressure, a first enclosure means made at least partially of a gas-permeable material, said container means and the articles to be sterilized being disposed in and sealed within said first enclosure means, said container means while in said sealed first enclosure means being manipulatable to release gaseous sterilant into said sealed first enclosure means, a second enclosure means in which said first enclosure means is disposed, said first enclosure means being constructed such that the sterilant released into said first enclosure means from said container means diffuses through said gas-permeable material of said first enclosure means into said second enclosure means at a rate for establishing sterilizing conditions in said first enclosure means during a sterilizing cycle to thereby effect sterilization of articles in said first enclosure means, a moisture-releasing humidifying means having a vapor-permeable cover disposed within said sealed first enclosure means for releasing moisture into said sealed first enclosure means during said sterilization cycle, and regulating means comprising an exhaust system operable to exhaust the sterilant gas from said second enclosure means to minimize the amount of sterilant gas in said second enclosure means.

2. Apparatus according to claim 1, wherein said regulating means comprises air-inlet means on said second enclosure means for admitting air into said second enclosure means.

3. Apparatus according to claim 2, wherein said exhaust system comprises an exhaust conduit leading from said second enclosure means, and an exhaust valve in said exhaust conduit operable between open and closed positions, said air-inlet means having an air inlet valve operable between open and closed positions, and interconnect means interconnecting said air inlet and exhaust valves such that said air inlet and exhaust valves operate together as an operable unit such that when one of said valves is in its closed position the other valve is also in its closed position and when one of said valves is in its open position, the other of said valves is in its open position.

4. Apparatus according to claim 3, wherein said exhaust valve has a movable valve element and a seat, said movable valve element having at least one portion spaced from said seat when said exhaust valve is in its said closed position to provide a flow passage through said exhaust valve when said exhaust valve is in said closed position, whereby the exhaust system continues exhausting said second enclosure means through said exhaust conduit while said air inlet valve and said exhaust valve are each in their closed positions.

5. Apparatus according to claim 1, wherein said second enclosure means comprises circulating means for circulating the gaseous sterilant within said second enclosure means.

6. Apparatus according to claim 1, wherein said second enclosure means comprises controlled heating means for heating and controlling the temperature within said second enclosure means.

7. Apparatus according to claim 1 further comprising a sterilization indicator means in said first enclosure means, said first enclosure means being made at least partially of a transparent material so that said sterilization indicator is viewable through said transparent material while disposed in said first enclosure means.

8. Apparatus according to claim 1, wherein said container means comprises an enclosure made of paper in which a glass ampule is disposed, said glass ampule being fracturable to release gaseous sterilant into said paper enclosure.

9. A method of sterilizing articles in an enclosed work area comprising the steps of containing a volatile sterilant within a sealed container, disposing said sealed container along with the articles to be sterilized and a moisture-releasing humidifying device having a vapor-permeable cover within a first enclosure made at least partially of a gas-permeable membrane, sealing said first enclosure, disposing said sealed first enclosure within a second enclosure, effecting a sterilizing cycle by releasing said sterilant from said sealed container into said first enclosure in gaseous form, passing said sterilant gas into said second enclosure by diffusion through said gas-permeable membrane while maintaining sterilizing conditions in said first enclosure during a sterilizing cycle to thereby effect sterilization of said articles in said first enclosure, releasing moisture from said moisture-releasing humidifying device into said sealed first enclosure during said sterilizing cycle, and regulating the gaseous conditions within said second enclosure to minimize the amount of sterilant gas in said second enclosure, thereby providing for minimized residue sterilant in said enclosed work area in which said second enclosure is disposed.

10. A method according to claim 9, wherein said step of effecting a sterilizing cycle by releasing said sterilant gas into said first enclosure in gaseous form is performed just prior to disposing said first enclosure into said second enclosure.

11. A method according to claim 9 further comprising maintaining the temperature of said second enclosure at about 50° C.

12. A method according to claim 9 further comprising effecting a purge cycle of said second enclosure by exhausting the gaseous medium from said second enclosure while simultaneously introducing air into said second enclosure.

13. A method according to claim 12, wherein said purging cycle is performed after said sterilizing cycle.

14. A method according to claim 9 further comprising circulating the gaseous sterilant within said second enclosure.

15. A method according to claim 9 further comprising effecting pre-treatment of said articles to be sterilized by additional steps which are performed after the step of sealing the first enclosure and prior to the step of releasing the sterilant from said sealed container, said additional steps comprising heating said sealed first enclosure to effect accelerated evaporation of moisture from said moisture-releasing humidifying device, and subsequently cooling said sealed first enclosure such that the sealed enclosure is saturated with moisture, said sealed first enclosure being subsequently subjected to said step of effecting said sterilizing cycle by releasing said sterilant from said sealed container into said first enclosure in gaseous form.

16. A method according to claim 15, wherein said additional step of heating said sealed first enclosure comprises heating said sealed first enclosure to about 50° C. in said second enclosure.

17. A method according to claim 16, wherein said additional step of cooling said sealed first enclosure comprises exposing said first enclosure to the ambient atmosphere.

18. A method according to claim 15, wherein said additional heating step comprises heating for about 4 hours.

19. A method according to claim 15, wherein said additional cooling step comprises cooling for about 4 hours.

20. A method according to claim 9 further comprising evacuating the air from said first enclosure before sealing said first enclosure.

21. A method according to claim 9 further comprising disposing a sterilization indicator in said first enclosure, said first enclosure being made at least partially of a transparent material to permit viewing of said sterilization indicator in said sealed first enclosure.

22. A method according to claim 9 further comprising disposing said sealed container within a paper enclosure, and sealing said paper enclosure with the sealed container disposed therein within said first enclosure.

* * * * *